(12) United States Patent
Launay et al.

(10) Patent No.: US 6,673,825 B2
(45) Date of Patent: Jan. 6, 2004

(54) URAZOLE COMPOUNDS USEFUL AS ANTI-INFLAMMATORY AGENTS

(75) Inventors: Michele Launay, Rueil Malmaison (FR); Dominique Potin, Epone (FR); Magali Jeannine Blandine Maillet, Suresnes (FR); Eric Antoine Nicolai, Rueil Malmaison (FR); Edwin J. Iwanowicz, Cranbury, NJ (US); T. G. Murali Dhar, Newtown, PA (US)

(73) Assignees: Bristol-Myers Squibb Co., Princeton, NJ (US); Cerep SA, Rueil-Malmaison (FR)

(*) Notice: Subject to any disclaimer, the term of this patent is extended or adjusted under 35 U.S.C. 154(b) by 0 days.

(21) Appl. No.: 10/152,117

(22) Filed: May 21, 2002

(65) Prior Publication Data

US 2003/0013745 A1 Jan. 16, 2003

Related U.S. Application Data

(60) Provisional application No. 60/292,384, filed on May 21, 2001.

(51) Int. Cl.$^7$ .................. A61K 31/4196; C07D 249/12; C07D 249/16
(52) U.S. Cl. ..................................... 514/383; 548/262.4
(58) Field of Search ........................ 548/262.4; 514/383

(56) References Cited

PUBLICATIONS

Davies et al., J. Chem. Soc., Perkins Trans. 1 (1976), (22), pp. 2390–2394.*
Wagener et al., J. Org. Chem. (1972), 37(9), pp. 1454–1456.*
Hall et al., J. Org. Chem. (1983), 48(6), pp. 822–826.*
Solomonov et al., J. Org. Chem. USSR (Engl. Transl.), 1980, pp. 1419–1423.*

* cited by examiner

Primary Examiner—Laura L. Stockton
(74) Attorney, Agent, or Firm—Anastasia P. Winslow; Laurelee A. Duncan

(57) ABSTRACT

Urazole compounds having the formula (I),

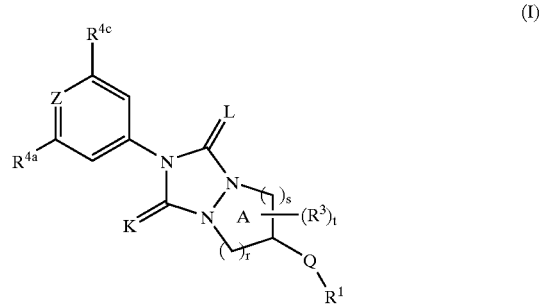

or pharmaceutically-acceptable salts thereof, are effective as anti-inflammatory or immunosuppressive agents, wherein L and K are O or S; Q is a linker such as —O—, —S—, C(=O), and so forth, $R^1$ is an aryl or heteroaryl group, and $R^3$, $R^{4a}$, $R^{4c}$, Z, r, s and t are as defined in the specification.

20 Claims, No Drawings

URAZOLE COMPOUNDS USEFUL AS ANTI-INFLAMMATORY AGENTS

RELATED APPLICATIONS

This application claims the benefit of U.S. Provisional Application No. 60/292,384, filed May 21, 2001, which is incorporated herein by reference.

FIELD OF THE INVENTION

The present invention relates to urazole compounds, pharmaceutical compositions containing them, and methods of using such compounds in treating inflammatory or immune disease.

BACKGROUND OF THE INVENTION

Cells adhere to other cells and to substrates through specific, regulated processes that are critical to various biological functions. The proper functioning of the immune system is dependent upon adhesive interactions and cell migration. A key event in an immune response involves the migration of leukocytes to a disease site. During an inflammatory response, leukocytes are recruited to the site of injury and extravasated by a series of cellular interactions involving cell—cell and cell-substrate adhesion.

One family of molecules that serve an important adhesive function are integrins. Integrins are expressed on cell surfaces and function in cell—cell and cell-substrate adhesion. Integrins are alpha-beta heterodimers: each integrin has an alpha ($\alpha$) subunit non-covalently binded to a beta ($\beta$) subunit. When activated, integrins bind to extracellular ligands and induce adhesion (the expression of integrins on a cell surface alone is inadequate for adhesion—they must be activated to become adhesive). The integrin activation state is transient, such that there is a rapid flux between adhesive and non-adhesive states which is important for cell movement, e.g., a cell is endowed with the ability to rapidly adhere to various cell surfaces and matrices and migrate among cells and tissue.

There are four known integrins having a $\beta_2$ or CD18 subunit which comprise the CD11/CD18 integrin subfamily, namely, Lymphocyte Function-associated Antigen 1 (LFA-1) (CD 11a/CD18 or $\alpha_L\beta_2$); Macrophage Antigen 1 (Mac-1) (CD11b/CD18 or $\alpha_M\beta_2$); p150,95 (CD11c/CD18 or $\alpha_x\beta_2$); and $\alpha_D\beta_2$. The CD11/CD18 family of integrins are also referred to as Leukointegrins as they are expressed on the surface of various leukocyte cells, and they mediate a number of inflammation-related cellular interactions. See Diamond et al., "*The Dynamic Regulation of Integrin Adhesiveness,*" Current Biology, Vol. 4 (1994) at pp. 506–532.

Ligands to LFA-1 and Mac-1 comprise the intercellular adhesion molecule (ICAM) ICAM-1. LFA-1, the primary CD11/CD18 integrin, also binds with ICAM-2 and ICAM-3. ICAMs are found on endothelium cells, leukocytes, and other cell types, and their interaction with CD11/CD18 integrins is critical to immune system function. The interaction between the CD18 integrins, particularly LFA-1, and ICAMs mediates antigen presentation, T-cell proliferation, and adhesion between the endothelium and activated leukocytes which is necessary for leukocytes to migrate from the circulatory system into tissue. A condition termed "Leukocyte Adhesion Deficiency" has been identified in patients having a severe deficiency in CD18 integrins. These patients are unable to mount a normal inflammatory or immune response; they suffer from disorders such as recurrent infections, poor wound healing, granulocytosis, progressive periodontitis, and umbilical cord separation. See Anderson et al., "*Leukocyte LFA-1, OKMI, p150,95 Deficiency Syndrome: Functional and Biosynthesis Studies of Three Kindreds,*" Fed. Proc., Vol. 44 (1985), pp. 2671–2677.

While sufficient levels of CD18 integrins interacting with ICAMs are needed to mount a normal immune response, significant cellular and tissue injury can result in chronic inflammatory states where there is an inappropriate influx of leukocytes to the disease site. Continuous recruitment of leukocytes from blood vessels into inflamed tissue, as in chronic inflammatory states, can perpetuate tissue injury and lead to excessive fibrous repair and autoimmune disease. Thus, inhibition of the interaction between LFA-1 and/or Mac-1 and their ICAMs can be advantageous in treating inflammatory or immune disease. For example, monoclonal antibody blockade of either ICAM or LFA-1 has been shown to prevent the migration of leukocytes into tissue and the subsequent development of inflammatory disease in animal models of rheumatoid arthritis, inflammatory bowel disease, and pulmonary inflammation (e.g., asthma). Knockout mice deficient in ICAMs have reduced susceptibility to induced arthritis, ischemia injury, impaired lung inflammatory responses, and increased tolerance to transplantations (e.g. heart grafts). See Anderson, supra. Antibodies blocking the ICAM-LFA-1 interaction reportedly suppress cardiac allograft rejection and islet cell xenograft rejection in animal models. See Gorski, "*The Role of Cell Adhesion Molecules in Immunopathology,*" Immunology Today, Vol. 15 (1994), at pp. 251–255.

Compounds inhibiting CD18 integrins, ICAMs, and/or the LFA-1:ICAM interaction could potentially demonstrate a wide range of utilities in treating inflammatory or immune diseases. Blocking LFA-1 reportedly inhibits the influx of leukocytes in almost every system, including the skin, peritoneum, synovium, lung, kidney and heart, and blocking ICAM-1 would be expected to have similar effects. Also, present therapies for many inflammatory or immune diseases have drawbacks. There is an interest in providing consumers with drugs having increased effectiveness and fewer side effects. For example, current treatments for asthma include $\beta_2$-agonists, inhaled corticosteroids, and $LTD_4$ antagonists. However, $\beta_2$-agonists have limited efficacy and inhaled corticosteroids raise safety concerns. To treat psoriasis, current therapies include PUVA, methotrexate, cyclosporin A, and topical treatments. The first three of those therapies raise toxicity issues over long-term (6–9 month) use, whereas topical treatments have limited efficacy. Additionally, these treatments typically are applied only in response to flares and not as a prophylaxis measure.

Accordingly, there is great interest in developing Leukointegrin or ICAM antibodies and antagonists of Leukointegrins and/or ICAMs. Compounds that reportedly inhibit LFA-1/ICAM for use as anti-inflammatory agents include thiadiazole-based compounds (see Intern. Pub. No. WO 99/20,618, "*Thiadiazole Amides Useful as Anti-Inflammatory Agents*" filed by Pharmacia & Upjohn Co.; and WO 99/20,617, also to Pharmacia and Upjohn); and thiazole compounds linked to phenyl and pyrazole rings (Sanfilippo et al., "*Novel Thiazole Based Heterocycles as Inhibitors of LFA-1/ICAM-1 Mediated Cell Adhesion,*" J. Med. Chem. Vol. 38 (1995) at pp.1057–1059). Small molecules that reportedly are antagonists to the binding of ICAMs with CD18 integrins include various benzylamines and 2-bromobenzoyltryptophan compounds (see Intern. Pub. No. WO99/49,856, "*Antagonists for Treatment of*

CD11/CD18 Adhesion Receptor Mediated Disorders," filed by Genentech, Inc.), and 1-(3,5 dichlorophenyl) imidazolidines (see Intern. Pub. No. WO98/39303, "Small Molecules Useful in the Treatment of Inflammatory Disease," filed by Boehringer Ingelheim Pharmaceuticals, Inc. See also Boehringer patent applications WO 01/07052, WO 01/07048, WO 01/07044, WO 01/06984, and WO 01/07440). Hydantoin compounds effective as LFA-1/ICAM antagonists are described in U.S. patent application Ser. Nos. 60/250,486 and 60/250,653, filed Dec. 1, 2000, by the same inventors herein and assigned to the present assignees. Hydantoin compounds are also disclosed in Intern. Pub. No. WO 01/30781 A2 (published May 3, 2001) to Tanabe Seiyaku Co. Ltd, "Inhibitors of $\alpha_L\beta_2$ Mediated Cell Adhesion."

As may be appreciated, those in the field of pharmaceutical research continue to seek new compounds and compositions for treating inflammatory or immune disease such as inhibitors of Leukointegrins and/or ICAMs. Particularly in the area of immune response, many individuals respond differently to different drugs. Thus, there is an interest in providing consumers not only with pharmaceutical compounds and compositions demonstrating increased effectiveness and reduced side-effects but also different structures or mechanisms of action to provide consumers with a choice of options. The instant invention is directed to urazole compounds that are effective as antagonists of Leukointegrins and/or ICAMs. Urazole compounds for use as herbicides are disclosed in WO 00/13508 to Ishihara Sangyo Kaisha, Ltd, published Mar. 16, 2000. See also WO 00/01700 and U.S. Pat. No. 5,109,014 (disclosing urazole compounds useful as herbicides or pesticides).

Each of the patents, patent applications and publications referenced above and hereinafter is incorporated herein by reference.

SUMMARY OF THE INVENTION

The present invention provides compounds useful in treating inflammatory or immune disease having the formula (I):

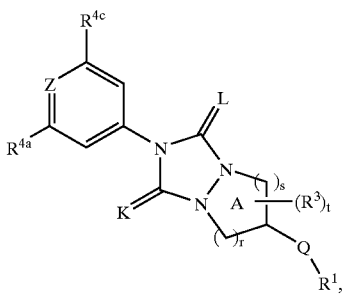

or pharmaceutically-acceptable salts thereof, in which:

L and K, taken independently, are O or S;

Q is —O—, —$NR^2$—, —S—, —C(=O)—, —$CO_2$—, —OC(=O), —$NR^2C$(=O)—, —C(=O)$NR^2$—, —N$R^2CO_2$—, $C_{1-4}$alkylene, $C_{1-4}$substituted alkylene, $C_{1-4}$alkenylene, $C_{1-4}$substituted alkenylene, or optionally-substituted bivalent $C_{1-4}$alkoxy, $C_{1-4}$alkylthio, $C_{1-4}$aminoalkyl, $C_{0-4}$sulfonyl, $C_{0-4}$sulfonamide, $C_{1-4}$acyl, or $C_{1-4}$alkoxycarbonyl;

Z is N or $CR^{4b}$;

$R^1$ is selected from —$(CH_2)_n$aryl and —$(CH_2)_n$heteroaryl, wherein the aryl and heteroaryl groups are optionally substituted;

$R^2$ is hydrogen or $C_{1-4}$alkyl;

$R^3$ is attached to any available carbon atom of ring A and at each occurrence is independently selected from halogen, alkyl, substituted alkyl, alkenyl, nitro, S(O)$_q$$R^8$, $NR^8SO_2R^9$, $SO_2NR^8R^9$, $A_1$—CN, $A_1$—$OR^8$, $A_1$—$NR^8R^9$, $A_1$—C(=O)$R^8$, $A_1$—OC(=O)$R^8$, $A_1$—OC(=O)$NR^8R^9$, $A_1$—$NR^8C$(=O)$R^9$, $A_1$—$NR^8C$(=O)$OR^9$, $A_2$—$CO_2R^8$, and $A_2$—C(=O)$NR^8R^9$; or where $R^3$ is attached to a carbon atom other than the Q—$R^1$ substituted carbon atom, $R^3$ may be oxo (=O);

$A_1$ is a bond, —$C_{1-4}$alkylene-, —NHC(=O)—, or —NHC(=O)$C_{1-4}$alkylene-;

$A_2$ is a bond, —$C_{1-4}$alkylene-, —NHC(=O)—, —NHC(=O)$C_{1-4}$alkylene-, —C(=O)— or —C(=O)$C_{1-4}$alkylene-;

$R^{4a}$, $R^{4b}$ and $R^{4c}$ are independently selected from hydrogen, halogen, alkyl, substituted alkyl, alkenyl, substituted alkenyl, nitro, cyano, $OR^6$, $NR^6R^7$, $NR^6C$(=O)$R^7$, $CO_2R^6$, C(=O)$R^6$, —C(=O)$NR^6R^7$, and optionally-substituted aryl, heteroaryl, cycloalkyl, and heteroaryl;

$R^6$ and $R^7$ (i) selected independently of each other are hydrogen, alkyl, substituted alkyl, substituted alkenyl, alkoxy, aminoalkyl, or optionally-substituted cycloalkyl, aryl, heteroaryl, or heterocyclo; or (ii) taken together form a heterocyclo;

$R^8$ and $R^9$ (i) selected independently of each other are hydrogen, alkyl, substituted alkyl, alkenyl, substituted alkenyl, alkoxy, or optionally-substituted cycloalkyl, aryl, heteroaryl, or heterocyclo; or (ii) taken together form a heterocyclo;

n is 0, 1, 2, 3 or 4;

q is 0, 1, or 2;

r and s are 0, 1, or 2, provided that r and s are not both zero such that ring A is a saturated, 4 to 7-membered monocyclic heterocyclo; and t is 0, 1, or 2.

The present invention is also directed to pharmaceutical compositions useful in treating immune or inflammatory diseases comprising compounds of formula (I), or pharmaceutically-acceptable salts thereof, and pharmaceutically-acceptable carriers or diluents. The invention also relates to methods of treating immune or inflammatory diseases comprising administering to a patient in need of such treatment a therapeutically-effective amount of a compound according to formula (I).

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo (e.g., trifluoromethyl), alkenyl, alkynyl, nitro, cyano, amino, oxo (=O), hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, —CO$_2$-alkyl, —C(=O)alkyl, —C(=O)aryl, —C(=O)NH$_2$, —C(=O)NH(alkyl), —C(=O)NH(cycloalkyl), —C(=O)N(alkyl)$_2$, —NH—CH$_2$—CO$_2$H—NH—CH(alkyl)-CO$_2$H, —NH—CH$_2$—CO$_2$-alkyl, —NH—CH(alkyl)-CO$_2$-alkyl, =N—OH, =N—O-alkyl, aryl, heteroaryl, heterocyclo, cycloalkyl, and substituted cycloalkyl, including phenyl, benzyl, phenylethyl, phenyloxy, and phenylthio. When a substituted alkyl includes an aryl, heterocyclo, or heteroaryl substituent, said ringed systems are as defined below and thus may have zero, one, two, or three substituents, also as defined below.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where one of the substituents is aryl, such as benzyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkoxy" refers to an alkyl or substituted alkyl group as defined above having one, two or three oxygen atoms (—O—) in the alkyl chain. For example, the term "alkoxy" includes the groups —O—C$_{1-12}$alkyl, —C$_{1-6}$alkylene-O—C$_{1-6}$alkyl, —C$_{1-4}$alkylene-O—C$_{1-4}$alkylene-O—C$_{1-4}$alkyl, O—C$_{1-4}$alkylene-O—C$_{1-4}$alkylene-O—C$_{1-4}$alkyl, and so forth.

The term "thioalkyl" or "alkylthio" refers to an alkyl or substituted alkyl group as defined above bonded through one or more sulfur (—S—) atoms. For example, the term "thioalkyl" or "alkylthio" includes the groups —S—C$_{1-12}$alkyl, —S—C$_{1-6}$alkylene-S—C$_{1-6}$alkyl, etc.

The term "aminoalkyl" refers to an alkyl or substituted alkyl group as defined above bonded through one or more nitrogen (—NR—) atoms. For example, the term "aminoalkyl" includes the groups —NR—C$_{1-12}$alkyl, —NR—C$_{1-6}$alkylene-NR—C$_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent C$_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_2$)$_2$. A lower aminoalkyl comprises an aminoalkyl having one to four carbon atoms. "Amino" refers to the group NH$_2$.

The alkoxy, thioalkyl, or aminoalkyl groups may be monovalent or bivalent. By "monovalent" it is meant that the group has a valency (i.e., power to combine with another group), of one, and by "bivalent" it is meant that the group has a valency of two. Thus, for example, a monovalent alkoxy includes groups such as —O—C$_{1-12}$alkyl, —C$_{1-6}$alkylene-O—C$_{1-6}$alkyl, —C$_{1-4}$alkylene-O—C$_{1-4}$alkylene-O—C$_{1-4}$alkyl, whereas a bivalent alkoxy includes groups such as —O—C$_{1-12}$alkylene-, —C$_{1-6}$alkylene-O—C$_{1-6}$alkylene-, —C$_{1-4}$alkylene-O—C$_{1-4}$alkylene-O—C$_{1-4}$alkylene-, and so forth.

The term "acyl" refers to a carbonyl group

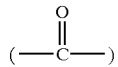

linked to an organic radical including an alkyl, alkenyl, alkynyl, aminoalkyl, substituted alkyl, substituted alkenyl, or substituted alkynyl, as defined above. The organic radical to which the carbonyl group is attached may be monovalent (e.g., —C(=O)-alkyl), or bivalent (e.g., —C(=O)alkylene, etc.)

The term "alkoxycarbonyl" refers to a carboxy or ester group

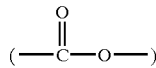

linked to an organic radical including an alkyl, alkenyl, alkynyl, aminoalkyl, substituted alkyl, substituted alkenyl, substituted alkynyl, or substituted aminoalkyl group, as defined above. The organic radical to which the carboxy group is attached may be monovalent (e.g., —CO$_2$-alkyl), or bivalent (e.g., —CO$_2$-alkylene, etc.)

The term "sulfonyl" refers to a sulphoxide group (i.e., —S(O)$_{1-2}$—) linked to an organic radical including an alkyl, alkenyl, alkynyl, aminoalkyl, substituted alkyl, substituted alkenyl, substituted alkynyl, or substituted aminoalkyl group, as defined above. The organic radical to which the sulphoxide group is attached may be monovalent (e.g., —SO$_2$-alkyl), or bivalent (e.g., —SO$_2$-alkylene, etc.) A —C$_0$-sulfonyl refers to the groups —S(O)$_{1-2}$—; a —C$_1$-sulfonyl refers to —CH$_2$S(O)$_{1-2}$— and —S(O)$_{1-2}$CH$_2$—; a —C$_2$-sulfonyl refers to —CH$_2$S(O)$_{1-2}$CH$_2$—, —S(O)$_{1-2}$CH$_2$CH$_2$—, —S(O)$_{1-2}$CH=CH—, and so forth.

The term "sulfonamide" refers to the group —S(O)$_2$NR$_a$R$_b$, wherein R$_a$ and R$_b$ may be hydrogen or alkyl, alkenyl, alkynyl, aminoalkyl, substituted alkyl, substituted alkenyl, substituted alkynyl, or substituted aminoalkyl group, as defined above. R$_a$ and R$_b$ may be monovalent or bivalent (e.g., —SO$_2$—NH-alkylene, etc.) When a subscript is used with a sulfonamide, as in —C$_{0-4}$-sulfonamide, it has the analogous meaning as referenced above for sulfonyl.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents selected from the group consisting of halo, alkyl, substituted alkyl (e.g., trifluoromethyl), alkenyl, alkynyl, nitro, cyano, amino, oxo, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)NH$_2$, —C(=O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$-alkyl, =N—OH, =N—O-alkyl, aryl, heteroaryl, heterocyclo, and a five or six membered ketal, e.g., 1,3-dioxolane or 1,3-dioxane.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl and 2-naphthyl, with phenyl being preferred. The term "aryl" includes such rings having zero, one, two or three substituents selected from the group consisting of halo, alkyl, substituted alkyl, alkenyl, alkynyl, nitro, cyano, amino, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)NH$_2$, —C(=O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$-alkyl, phenyl, benzyl, napthyl, phenylethyl, phenyloxy, phenylthio, cycloalkyl, substituted cycloalkyl, heterocyclo, and heteroaryl. Addtionally, when reference is made herein to optionally-substituted aryl groups as selections for $R^1$, $R^{4a}$ $R^{4b}$ and $R^{4c}$, such aryl groups may in addition to the foregoing substituents contain one or more substituents selected from $OR^c$, $NR^cR^d$, $CO_2R^c$, $C(=O)R^c$, $C(=O)NR^cR^d$, $NR^cC(=O)R^d$, $NR^cC(=O)OR^d$, $S(O)_{0-2}R^c$, $NR^cSO_2R^d$, $SO_2NR^cR^d$, —NHCH(alkyl)CO$_2R^c$, wherein $R^c$ and $R^d$ are (i) selected independently of each other are hydrogen, alkyl, substituted alkyl, substituted alkenyl, alkoxy, cycloalkyl, aryl, heteroaryl, or heterocyclo; or (ii) taken together form a heterocyclo which in turn may be optionally substituted as set forth below.

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halo, alkyl, substituted alkyl, alkenyl, alkynyl, nitro, cyano, amino, oxo, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)aryl, —C(=O)NH$_2$, —C(=O)NH(alkyl), —C(=O)NH(cycloalkyl), —C(=O)N(alkyl)$_2$, —NH—CH$_2$—CO$_2$H, —NH—CH$_2$—CO$_2$-alkyl, —NHCH(C$_{1-4}$alkyl)-CO$_2$H, —NHCH(C$_{1-4}$alkyl)CO$_2$-alkyl, aryl, heteroaryl, heterocyclo, =N—OH, =N—O-alkyl, and a five or six membered ketal, e.g., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, amino, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)NH$_2$, —C(=O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$-alkyl, phenyl, benzyl, phenylethyl, phenyloxy, phenylthio, cycloalkyl, substituted cycloalkyl, heterocyclo, and heteroaryl. Addtionally, when reference is made herein to optionally-substituted heteroaryl groups as selections for $R^1$, $R^{4a}$ $R^{4b}$ and $R^{4c}$, such heteroaryl groups may in addition to the foregoing substituents contain one or more substituents selected from $OR^c$, $NR^cR^d$, $CO_2R^c$, $C(=O)R^c$, $C(=O)NR^cR^d$, $NR^cC(=O)R^d$, $NR^cC(=O)OR^d$, $S(O)_{0-2}R^c$, $NR^cSO_2R^d$, $SO_2NR^cR^d$, —NHCH(alkyl)CO$_2R^c$, wherein $R^c$ and $R^d$ are (i) selected independently of each other are hydrogen, alkyl, substituted alkyl, substituted alkenyl, alkoxy, cycloalkyl, aryl, heteroaryl, or heterocyclo, except when attached to a sulfonyl group as in $S(O)R^c$ or $S(O)_2R^c$, then $R^c$ is not hydrogen; or (ii) taken together form a heterocyclo which in turn may be optionally substituted as set forth below.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

Throughout the specification, groups and substituents thereof may be chosen by one skilled in the field to provide stable moieties and compounds. For example, in compounds of formula (I), below,

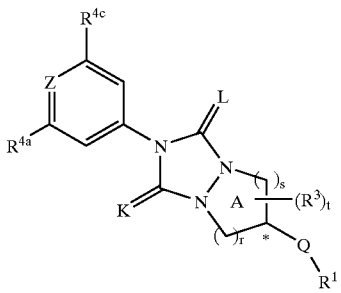

(I)

the substituent $R^3$ may be attached to any available carbon atom of the "A" ring, including the carbon atom to which the group $Q$—$R^1$ is attached. For ease of reference, this carbon atom (C—*) shall be referred to as the "$Q$—$R^1$ substituted carbon atom" (e.g., where "r" and "s" are both 1, the 6-position carbon atom will be the "$Q$—$R^1$ substituted carbon atom.") When Q comprises a heteroatom directly attached to ring A, advantageously any $R^3$ group attached to the $Q$—$R^1$ substituted carbon atom does not comprise a heteroatom directly attached to ring A, and vice-versa.

The compounds of formula (I) form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

Methods of Preparation

The compounds of the invention may be prepared by the exemplary processes described in the following reaction Schemes A to E. Exemplary reagents and procedures for these reactions appear hereinafter. Starting materials are commercially available or can be readily prepared by one of ordinary skill in the art. For all of the schemes, the groups Z, Q, K, L, $R^1$, $R^3$, $R^{4a}$, $R^{4b}$, and $R^{4c}$ are as described herein for a compound of formula (I), unless otherwise indicated. Groups designated R, X, and Y as well as solvents, temperatures, pressures, starting materials having the desired groups, and other reaction conditions, may be readily selected as appropriate by one of ordinary skill in the art.

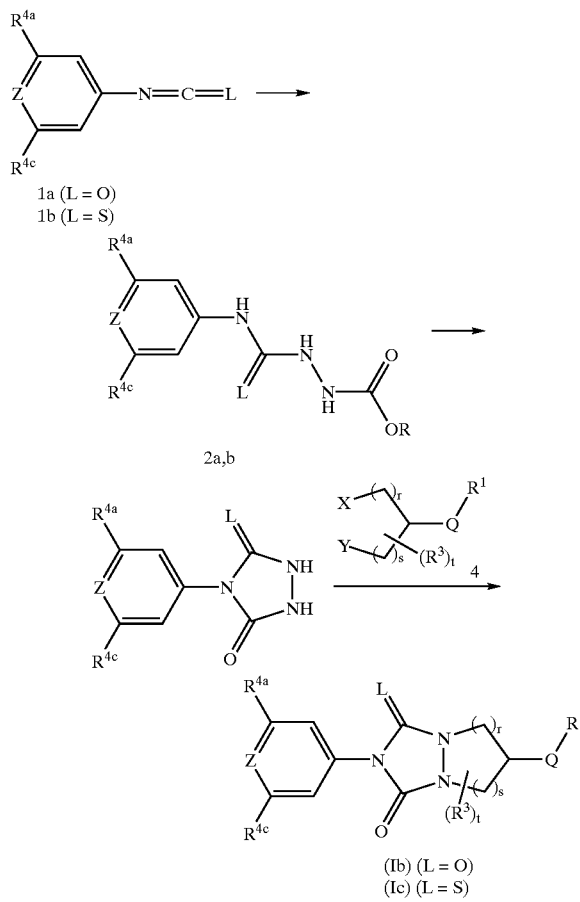

Isocyanate 1a is reacted with an alkyl carbazate to yield the alkoxycarbonyl semicarbazide 2a, which is cyclized with a base such as potassium carbonate, potassium hydroxide, sodium hydroxide, or sodium ethylate to give urazole 3a (see, e.g., Guzikowski et al., *J. Org. Chem.*, Vol. 48 [1983], at p. 2654). This compound is converted into its salt (sodium salt for example) and reacted with compound 4 having two leaving groups X and Y, to yield the desired compound of formula (Ib) (see, e.g., Mitsubishi Chemical Industries, Patent DE 2526358). Under the same conditions, isothiocyanate 1b gives 2b which is converted to the thioxo triazolone (Ic) via intermediate alkoxycarbonyl thiosemicarbazide 3b (see, e.g., Tisler et al. *Arch. Pharm.* (Weinheim), Vol. 292 [1959] at p. 90).

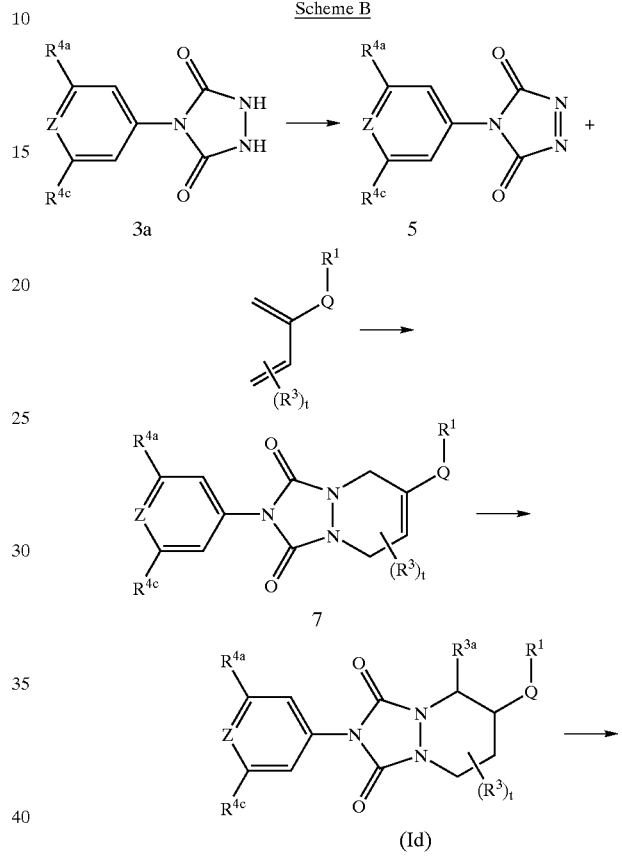

Six membered ring compounds can also be obtained as depicted in Scheme B. Urazole 3a is oxidized with a reagent such as tert-butyl hypochlorite in a solvent such as ethyl acetate to yield the triazoledione 5 (see, e.g., Hansen et al., *J. Chem. Soc. Perkin Trans.* 1, Vol. 22 [1999], at p. 3323). This compound is then condensed in a hetero Diels Alder reaction with a suitably substituted diene 6 to give compound 7 (see, e.g., Bernabeu et al. *Tetrahedron Lett.*, Vol. 37 [1996], at p. 3595). Reduction using, for example, hydrogen over a catalyst such as platinum or palladium in a solvent such as methanol or acetic acid leads to the desired compound of formula (Id) (see, e.g., Adams et al., *Synth. Commun.*, Vol. 18 [1988], at p. 2225).

Scheme C

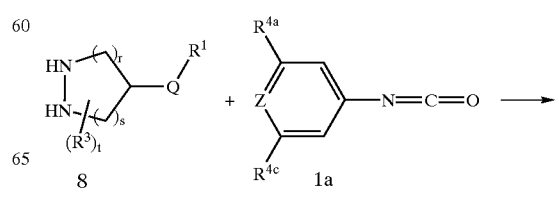

-continued

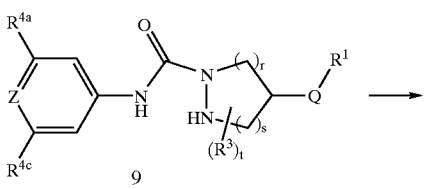

9

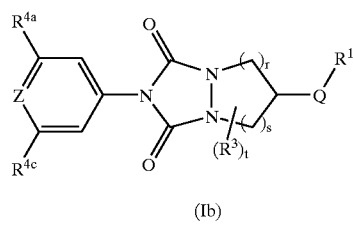

(Ib)

Alternatively, compound of formula (Ib) can also be obtained from the cyclic hydrazine 8 in the following manner: condensation of the hydrazine with an aromatic isocyanate 1a to yield 9 and cyclization with a reagent such as carbonyldiimidazole or ethyl chloroformate (see, e.g., Capuano et al., *Liebigs Ann. Chem.*, [1981], at 1361).

Scheme D

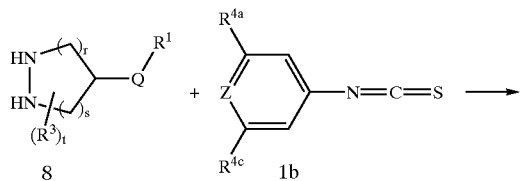

8       1b

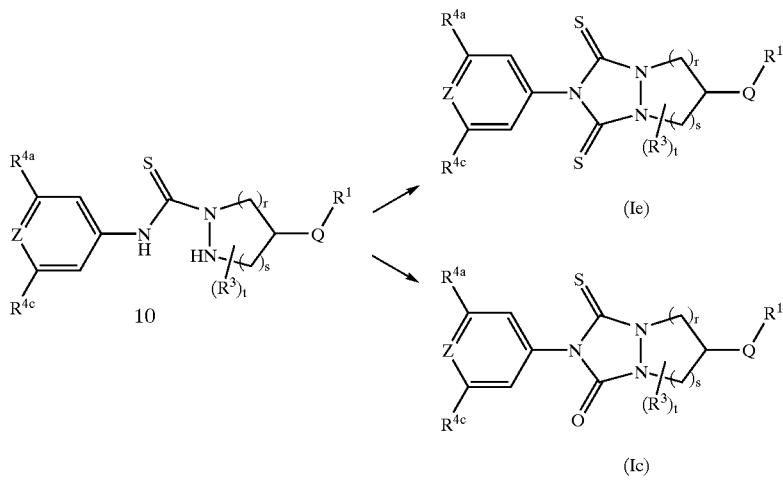

Triazole dithiones of formula (Ie) and thioxo triazolones of formula (Ic) are obtained in a similar way from cyclic hydrazine 8. Thus, reaction of hydrazine 8 with aryl isothiocyanate 1b leads to compound 10. The latter can be cyclized with a reagent such as thiocarbonyldiimidazole, thiophosgene or methylisothiocyanate to give the desired triazole dithione of formula (Ie) (see, e.g., Morgenstern et al., *Pharmazie*, Vol. 46 [1991], at 418–422, or *Pharmazie*, Vol. 49 [1994], at 489–492). Alternatively, reaction of 10 with a reagent such as a chloroformate, carbonyl diumidazole, phosgene or a phosgene equivalent yields the desired thioxo triazolone of formula (Ic) (see, e.g., Klemann et al., *Pharmazie*, Vol. 46 [1991], at 573–575).

Scheme E

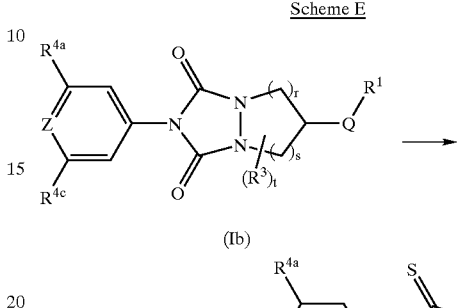

(Ib)

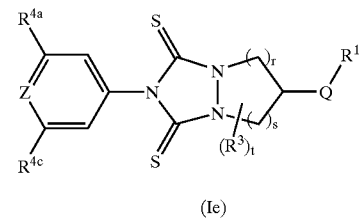

(Ie)

[1,2,4]Triazole-1,3-dithione of formula (Ie) can also be obtained from urazole of formula (Ib) by reaction with $P_2S_5$ or Lawesson's reagent in a solvent such as toluene or dioxane.

Preferred Compounds

Preferred compounds of this invention are those of formula (Ia):

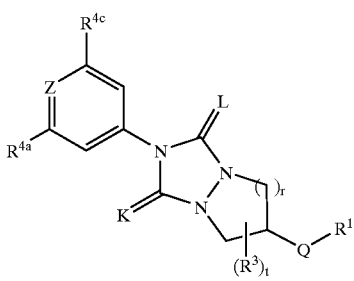

(Ia)

or a pharmaceutically-acceptable salt thereof, in which:

K and L are independently O or S;

Q is —O—, —NH—, —S—, —$CO_2$—, —C(=O)—, —OC(=O), —NHC(=O)—, —C(=O)NH—, —NHCO$_2$—, $C_{1-4}$alkylene, $C_{1-4}$substituted alkylene, $C_{1-4}$alkenylene, $C_{1-4}$substituted alkenylene, or optionally-substituted bivalent $C_{1-4}$alkoxy, $C_{1-4}$alkylthio, $C_{1-4}$aminoalkyl, $C_{0-4}$sulfonyl, $C_{0-4}$sulfonamide, $C_{1-4}$acyl, or $C_{1-4}$alkoxycarbonyl;

Z is N or $CR^{4b}$;

$R^1$ is aryl or heteroaryl optionally substituted with one to two substituents selected from halogen, alkyl, substituted alkyl, nitro, cyano, $OR^{10}$, $NR^{10}R^{11}$, $CO_2R^{10}$, C(=O)$R^{10}$, C(=O)$NR^{10}R^{11}$, $NR^{10}$C(=O)$R^{11}$, $NR^{10}$C(=O)$OR^{11}$, $S(O)_pR^{10}$, $NR^{10}SO_2R^{11}$, $SO_2NR^{10}R^{11}$, —NHCH(alkyl)$CO_2R^{10}$, aryl, cycloalkyl, and heteroaryl;

$R^3$ is attached to any available carbon atom of ring A and at each occurrence is independently selected from halogen, alkyl, substituted alkyl, alkenyl, nitro, $S(O)_q R^8$, $NR^8SO_2R^9$, $SO_2NR^8R^9$, $A_1$—CN, $A_1$—$OR^8$, $A_1$—$NR^8R^9$, $A_1$—C(=O)$R^8$, $A_1$—OC(=O)$R^8$, $A_1$—OC(=O)$NR^8R^9$, $A_1$—$NR^8$C(=O)$R^9$, $A_1$—$NR^8$C(=O)$OR^9$, $A_2$—$CO_2R^8$, and $A_2$—C(=O)$NR^8R^9$; or where $R^3$ is attached to a carbon atom other the Q—$R^1$ substituted carbon atom, $R^3$ may be oxo (=O);

$A_1$ is a bond, —$C_{1-4}$alkylene-, —NHC(=O)—, or —NHC(=O)$C_{1-4}$alkylene-;

$A_2$ is a bond, —$C_{1-4}$alkylene-, —NHC(=O)—, —NHC(=O)$C_{1-4}$alkylene-, —C(=O)— or —C(=O)$C_{1-4}$alkylene-;

$R^{4a}$ and $R^{4c}$ are halogen, alkyl, cyano, trifluoromethyl, or nitro;

$R^{4b}$ is hydrogen, halogen, alkyl, substituted alkyl, nitro, cyano, hydroxy, alkoxy, phenyloxy, —$CO_2H$, —C(=O)H, amino, NH(alkyl), N(alkyl)$_2$, $CO_2$alkyl, C(=O)alkyl, alkylthio, —C(=O)NH(CH$_2$)$_{1-4}$CO$_2$H, —C(=O)NH(CH$_2$)$_{1-4}$CO$_2$(alkyl), aryl, heteroaryl, or heterocycle, wherein each of the aryl, heteroaryl, and heterocycle groups are optionally substituted with one to two halogen, $C_{1-4}$alkyl, OMe, $CF_3$, CN, $OCF_3$, $CO_2H$, —C(=O)H, $CO_2$alkyl, or C(=O)alkyl;

$R^6$ and $R^7$ (i) selected independently of each other are hydrogen, alkyl, substituted alkyl, substituted alkenyl, alkoxy, or optionally-substituted cycloalkyl, aryl, heteroaryl, or heterocyclo; or (ii) taken together form a heterocyclo ring;

$R^8$ and $R^9$ (i) selected independently of each other are hydrogen, alkyl, substituted alkyl, substituted alkenyl, alkoxy, or optionally-substituted cycloalkyl, aryl, heteroaryl, or heterocyclo; or (ii) taken together form a heterocyclo ring;

$R^{10}$ and $R^{11}$ (i) selected independently of each other are hydrogen, alkyl, substituted alkyl, substituted alkenyl, alkoxy, or optionally-substituted cycloalkyl, aryl, heteroaryl, or heterocyclo; or (ii) taken together form a heterocyclo;

p and q are independently 0, 1, or 2;

r is 1 or 2; and t is 0, 1 or 2.

Further preferred are compounds according to formula (Ia), as defined immediately above, or pharmaceutically-acceptable salts thereof, in which $R^{4a}$ and $R^{4c}$ are halogen, nitro, haloalkyl, or haloalkoxy, most preferably halogen, and $R^{4b}$ is hydrogen. Advantageously, Q is —O—C(=O)— or bivalent alkoxy, preferably —O—CH$_2$—, and $R_1$ is phenyl optionally substituted with one to two substituents selected from halogen, cyano, nitro, haloalkyl, haloalkoxy, lower alkyl, —$CO_2H$, —C(=O)H, $CO_2$alkyl, and —C(=O)alkyl.

More preferred are compounds according to formula (Ib),

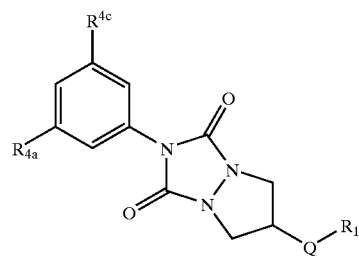

(Ib)

or pharmaceutically-acceptable salts thereof, in which:

Q is —OC(=O) or optionally-substituted bivalent $C_{1-4}$alkoxy;

$R^1$ is phenyl optionally substituted with one to two substituents selected from halogen, $C_{1-4}$alkyl, hydroxy, alkoxy, haloalkyl, haloalkoxy, cyano, nitro, —$CO_2H$, —C(=O)H, $CO_2$alkyl, and —C(=O)alkyl; and $R^{4a}$ and $R^{4c}$ are selected from halogen, trifluoromethyl, cyano, nitro, and $OCF_3$.

Most preferred are compounds according to formula (Ib), above, in which $R^{4a}$ and $R^{4c}$ are halogen (most preferably chloro); $R_1$ is

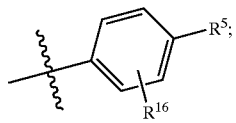

$R^5$ is halogen cyano, nitro, trifluoromethyl, or $OCF_3$, and $R^{16}$ is hydrogen, halogen, $C_{1-4}$alkyl, cyano, nitro, —$CO_2H$, —C(=O)H, $CO_2$alkyl, or —C(=O)alkyl.

Utility

The compounds and compositions of this invention are antagonists of LFA-1, Mac-1, and/or ICAMs. Thus, they are useful in treating various inflammatory diseases and disorders associated with the action of LFA-1, Mac-1, and/or ICAMs, particularly LFA-1:ICAM-1. The term "Leukointegrin/ICAM-associated condition" is used herein for ease of reference to refer to those diseases or disorders that are associated with the action or levels of LFA-1, Mac-1 and/or ICAM-1, ICAM-2, or ICAM-3. As used herein the term "treating" includes prophylactic and therapeutic uses and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The inventive compounds and compositions are useful for treating a wide range of conditions, as the action of LFA-1 and/or ICAMs is associated with the influx of leukocytes in almost every system, including the skin, peritoneum, synovium, lung, kidney and heart. The inventive compounds may be used to treat conditions resulting from a response of the specific immune system in a patient or the nonspecific immune system. Such conditions include, for example, graft vs host reactions and transplant rejection (e.g., kidney, liver, heart, lung, pancreas, bone marrow, cornea, small bowel, skin allografts, skin homografts and heterografts, etc.); psoriasis, organ-tissue autoimmune diseases (e.g., Raynaud's syndrome), autoimmune thyroiditis, dermatitis, multiple sclerosis, rheumatoid arthritis, insulin dependent diabetes mellitus, uveitis, inflammatory bowel disease including Crohn's disease and ulcerative colitis and systemic lupus erythematosus, adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infraction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, pulmonary fibrosis, atherosclerosis, meningitis, encephalitis, experimental autoimmune encephalomyelitis, Sjorgen's syndrome, and juvenile onset diabetes. The compounds of the present invention also may be used to treat allergic conditions such as eczema and asthma or as an adjunct to minimize toxicity with cytokine therapy in the treatment of cancers. In view of their inhibition activity, the compounds may be used to treat inflammatory conditions that involve the infiltration of T-cells and chronic inflammatory responses, hypersensitivity reactions, such as skin hypersensitivity reactions (including poison ivy and poison oak), immune responses associated with delayed hypersensitivity mediated by cytokines and T-lymphocyes, and metastases.

The compounds of this invention further have utility in treating hypogonadism, frailty, osteoporosis, sexual dysfunction, wasting, such as wasting syndromes associated with cancer and AIDS, and anemia. The compounds further have utility in treating cancers, including but not limited to cancers of the breast, brain, skin, ovary, endometrium, bladder, prostate, lung, colon, lymphatic system, liver and kidney. The compounds of the present invention are useful for conditions such as hirsutism, Alzheimer's disease, non-insulin dependent diabetes mellitus, acne, seborrhea, alopecia, fibroids, hyperpilosity, cachexia, polycystic ovarian syndrome, anorexia, contraception, drug withdrawal syndrome, pregnancy termination, and benign prostate hypertrophy. The compounds are further useful as antiangiogenic agents.

When used as anti-inflammatory agents, the compounds may be administered prior to the onset of, at, or after the initiation of inflammation. When used prophylactically, the compounds are preferably provided in advance of any inflammatory response or symptom (for example, prior to, at, or shortly after the time of an organ or tissue transplant but in advance of any symptoms or organ rejection). Administration of the compounds may prevent or attenuate inflammatory responses or symptoms.

The present invention thus provides methods for treating such conditions as those listed above, comprising administering to a subject in need thereof an effective amount of at least one compound of formula (I) or a salt thereof. Other therapeutic agents such as those described below may be employed in combination with the compounds of formula (I). In the methods of the present invention, such other therapeutic agent(s) may be administered prior to, simultaneously with, or following the administration of the inventive compounds.

The present invention also provides pharmaceutical compositions capable of treating the Leukointegrin/ICAM-associated conditions and above-described diseases and disorders. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (A VICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a patient of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and the particular condition sought to be treated and its severity. Preferred subjects for treatment include animals, most preferably mammalian species such as humans, and domestic animals such as dogs, cats, horses, and the like, subject to Leukointegrin/ICAM associated conditions and/or subject to any of the above-referenced diseases and disorders.

The inventive compounds and compositions may be employed alone or in combination with each other and/or other suitable therapeutic agents useful in treating Leukointegrin/ICAM-associated conditions and diseases and disorders referenced above. Exemplary of such other therapeutic agents include corticosteroids, cyclosporin, methotrexate, CELLCEPT™ (mycophenolate mofetil), co-stimulation blockades, growth hormones, and growth hormone secretagogues. Additionally, the inventive compounds may be administered either alone or in combination with anti-cancer and cytotoxic agents and treatments useful in treating cancer or other proliferative diseases, for example, where the second drug has the same or different mechanism of action than the present compounds. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids and epipodophyllotoxins; topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may be used in conjunction with radiation therapy.

Representative examples of these classes of anti-cancer and cytotoxic agents that may be used in combination with the inventive compounds include but are not limited to paclitaxel, cisplatin, carboplatin, doxorubicin, carminomycin, daunorubicin, idarubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine, mechlorethamine hydrochloride, cyclophosphamide, chlorambucil, ifosfamide, busulfan, carmustin, lomustine, semustine, streptozocin, thiotepa, dacarbazine, methotrexate, thioguanine, fludarabine, pentastatin, cladribin, cytarabine, bleomycin, mitomycin C, actinomycin D, safracins, saframycins, quinocarcins, discodermolides, vinorelbine, tamoxifen, estramustine, flutamide, buserelin, leuprolide, pteridines, diynes, levamisole, aflacon, interferon, interleukins, aldesleukin, filgrastim, sargramostim, rituximab, BCG, tretinoin, irinotecan, betamethasone, altretamine, and topotecan and any analogs or derivatives thereof.

Examples of anticancer and other cytotoxic agents that may be used in combination with the inventive compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The above other therapeutic agents, when employed in combination with the compounds of the present invention, may be used, for example, in those amounts indicated in the Physicians' Desk Reference (PDR) or as otherwise determined by one of ordinary skill in the art.

The inventive compounds have been tested in cell—cell assays and demonstrated activity consistent with inhibition of LFA-1 and/or ICAM-1.

Assays

H1-HeLa Adhesion Assay

H1-Hela cells were released from their growth flask using versene (Gibco, Grand Island, N.Y.). Following centrifugation, the cells were resuspended in growth medium: DMEM (Gibco), 10% fetal calf serum (Hyclone, Logan, Utah), 1% Pen-Strep (Gibco), and 1% L-glutamine (Gibco) and plated for growth at 5,000 cells/well in a 96-well plate.

The next day, HSB-2 cells were divided to $2\times10^5$/ml in growth medium: RPMI 1640 (Gibco), 10% FCS, 1% Pen-Strep, and 1% L-glutamine. The next day (day #3), the cells were centrifuged at 534×G for 8 minutes, washed, and resuspended in HBSS at $5\times10^7$/ml. Calcein-AM, 10 μM (Molecular Probes, Eugene, Oreg.) and 100 nM phorbol myristate acetate (SIGMA, St. Louis, Mo.) were added to the labeling and activation mix. Following incubation at 37° C. for 30 minutes, 10 ml of HBSS was added and the cells centrifuged as above. The cell pellet was then resuspended and counted.

While the HSB-2 cells were labeling, the medium was aspirated from the H1-HeLa cells and the plates washed once with HBSS, followed by the addition of 50 μl of HBSS. An additional 50 μl of HBSS containing compound solution, DMSO, or anti-CD18 antibody was then added to each well. To the H1-HeLa cells were added 200,000 HSB-2 cells/well in 100 μl, followed by incubation in the dark for 30 minutes. The wells were then washed three times to remove the unbound cells. A fluorescence plate reader was then used to determine the number of bound HSB-2 cells. The percent inhibition due to the compound was calculated using the vehicle control as 0% inhibition and the antibody blocked adhesion as 100% inhibition.

HUVEC Adhesion Assay

On day 1, human umbilical vein endothelial cells (HUVEC) (passage 3, Clonetics, San Diego, Calif.) were placed into a T-75 flask containing EGM bulletkit media (Clonetics) for growth.

When the HUVEC were 90% confluent (typically day 4), 96-well tissue culture plates were coated with 100 μl/well of 2.5 μg/ml mouse Type IV collagen (Gibco) diluted in 0.1 M acetic acid. Following incubation for at least three hours, the collagen was removed and the plate washed three times with HBSS (Gibco). The HUVEC flask was trypsinized, and HUVEC were plated on the collagen coated wells at 1250 cells/200 μl/well for use four days later. Twenty hours prior to use, the medium was removed and cells were stimulated with 200 μl of 1 μg/ml lipopolysaccharide (LPS, Sigma, St. Louis, Mo.) in EGM. When the cells were 90% confluent (typically day 8), the LPS-containing medium was removed, the wells were washed with HBSS, and 50 μl of HBSS was added to the wells. An additional 50 μl containing compound solution, DMSO or blocking anti-CD18 was then added to each well.

On day 7, HSB-2 cells were then divided to $2\times10^5$/ml in RPMI 1640 (Gibco), 10% FCS (Hyclone, Logan, Utah), 1% Pen-Strep (Gibco), and 1% L-glutamine (Gibco). The following day, the cells were centrifuged at 534×G for 8 minutes, washed, and resuspended in HBSS at $5\times10^7$/ml. For activation and labeling, calcein-AM, 10 μM (Molecular Probes, Eugene, Oreg.) and 100 nM phorbol myristate acetate (Sigma, St. Louis, Mo.) were added and the cells incubated at 37° C. for 30 minutes. Following the addition of 10 ml of HBSS, the cells were centrifuged, resuspended, and counted.

To the HUVEC cells were added 200,000 labeled and activated HSB-2 cells/well in 100 μl, followed by incubation in the dark for 30 minutes. To remove unbound cells, the wells were washed three times with HBSS. A fluorescence plate reader was used to determine the number of HSB-2 cells bound. The percent inhibition due to the compound was calculated with the vehicle control set at 0% inhibition and the antibody-blocked adhesion set at 100% inhibition.

The following Examples illustrate embodiments of the invention and are not intended to limit the scope of the claims.

EXAMPLES

The following Examples illustrate embodiments of the inventive compounds and starting materials, and are not intended to limit the scope of the claims. For ease of reference, the following abbreviations are used herein:

Abbreviations

Me=methyl
MeOH=methanol
Et=ethyl
EtOH=ethanol
Bn=benzyl
t-Bu=tert-butyl
Boc=tert-butoxycarbonyl
CBZ=carbobenzyloxy
CDI=1,1'-carbonyldiimidazole
DCC=dicyclohexyl carbodimide
DCM=dichloromethane
DEAD=diethyl azodicarboxylate
DIAD=diisopropyl azodicarboxylate
DMAP=dimethylaminopyridine
DMF=dimethyl formamide
EDC (or EDC.HCl) or EDCI (or EDCI.HCl) or EDAC=3-ethyl-3'-(dimethylamino)propyl-carbodiimide hydrochloride (or 1-(3 dimethylaminopropyl)-3-ethylcarbodiimide hydrochloride)
EtOAc=ethyl acetate
FMOC=9-fluorenylmethyl carbamate
HOBT=1-hydroxybenzotriazole hydrate
KOH=potassium hydroxide
KHMDS=potassium bis(trimethylsilyl)amide
LDA=lithium diisopropylamide
LiHMDS=lithium hexamethyldisilazane
$NaBH(OAc)_3$=sodium triacetoxyborohydride
Pet.=petroleum
Ph=phenyl
$Ph_3P$=triphenylphosphine
TEA=triethylamine
TFA=trifluoroacetic acid
THF=tetrahydrofuran
L=liter
mL=milliliter
μL=microliter
g=gram(s)
mg=milligram(s)
RT=room temperature
bp=boiling point
HPLC=high performance liquid chromatography
Mp=melting point

Preparation 1

1-Bromo-4-(2-bromo-1-chloromethyl-ethoxymethyl)-benzene

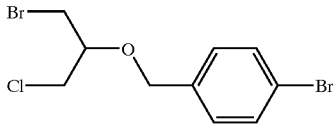

A mixture of 4-bromobenzylbromide (90 g, 0.36 mol), epichlorhydrin (34 g, 0.37 mol) and mercuric chloride (0.05 g, 0.18 mmol) was heated for 11 h at 155° C. After cooling, the resulting oil was distilled under reduced pressure to yield the above compound as a colorless oil (68.7 g, bp=180° C. (2 mm Hg)). $^1$H NMR (CDCl$_3$): 7.45–7.55 (2H, d, J=8.8 Hz), 7.2–7.3 (2H, d, J =8.8 Hz), 4.55 (2H, s), 3.65–3.95 (3H, m), 3.5–3.6 (2H, m).

Preparation 2

4-(3,5-Dichlorophenyl)-1-(methoxycarbonyl) semicarbazide

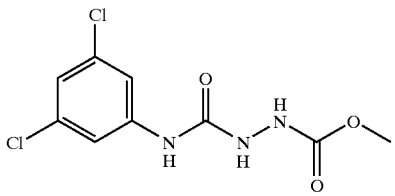

3,5-Dichlorophenyl isocyanate (25 g, 133 mmol) was added dropwise to a cooled solution of methyl hydrazinocarboxylate (12 g, 133 mmol) in dry toluene (250 ml), with the temperature in the reaction flask maintained below 10° C. during the addition. After 28 h at RT, the precipitate was filtered, washed with toluene and isopropyl ether, and dried to yield the above compound as a white solid (30.3 g, mp=246° C.).

Preparation 3

4-(3,5-Dichlorophenyl)-[1,2,4]triazolidine-3,5-dione

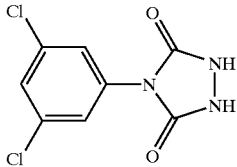

A suspension of 4-(3,5-dichlorophenyl)-1-(methoxycarbonyl)semicarbazide (30.3 g, 109 mmol) (Preparation 2) in KOH (54.5 ml, 4M) was heated under reflux for 1 h. After cooling to RT, the insoluble material was discarded and the filtrate acidified to pH 1–2. The precipitate was filtered, washed with water and pentane, and oven dried to yield the above compound as a white solid (27 g, mp=260° C.). $^1$H NMR (DMSO-d$_6$): 10.80 (2H, s), 7.66 (3H, m).

Preparation 4

4-(3,5-Dichlorophenyl)-[1,2,4]triazolidine-3,5-dione Disodium Salt

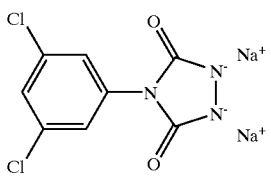

To a solution of sodium methylate [prepared by addition of sodium (5.05 g, 220 mmol) to MeOH (300 ml)], was added 4-(3,5-dichlorophenyl)-[1,2,4]triazolidine-3,5-dione (27 g, 110 mmol) (Preparation 3). After 2 h at RT, the solvent was evaporated to yield the above disodium salt as a white solid (31.1 g, mp>250° C.).

Preparation 5

6-(tert-Butyl-dimethylsilyloxy)-2-(3,5-dichlorophenyl)-dihydro-pyrazolo[1,2-α][1,2,4]triazole-1,3-dione

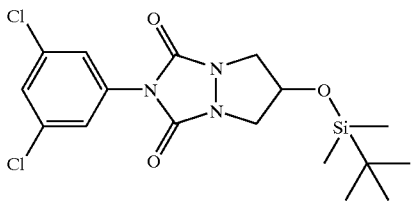

A mixture of the disodium salt of 4-(3,5-dichlorophenyl)-[1,2,4]triazolidine-3,5-dione (7.65 g, 26.4 mmol) (Preparation 4) and 1,3-dibromo-2-(tert-butyldimethylsilyloxy)propane [11.7 g, 35.2 mmol; prepared according to Axenrod, et al. *J. Org. Chem.*, Vol. 60 (1995), at pp. 1959–64] in DMF (160 ml) was heated under reflux for 2 h 45 min. The solvent was then removed under vacuum, and the resulting solid was chromatographed over silica gel (CH$_2$Cl$_2$) to yield the above compound as a white solid (2 g, mp=129° C.). $^1$H NMR (CDCl$_3$): 7.51 (2H, m), 7.35 (1H, m), 4.52 (1H, br s), 3.95 (2H, d, J=11.6 Hz), 3.49 (2H, dd, J$_1$=11.6 Hz, J$_2$ =2 Hz), 0.81 (9H, s), 0.09 (6H, s).

Preparation 6

2-(3,5-Dichlorophenyl)-6-hydroxy-dihydro-pyrazolo [1,2-α][1,2,4]triazole-1,3-dione

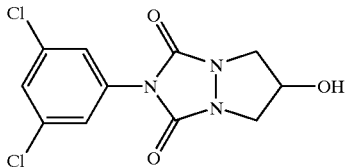

A solution of 6-(tert-Butyl-dimethylsilyloxy)-2-(3,5-dichlorophenyl)-dihydro-pyrazolo[1,2-α][1,2,4]triazole-1,3-dione (1.9 g, 4.56 mmol) (Preparation 5) in a mixture of 50% hydrofluoric acid (2 ml) and acetonitrile (80 ml) was heated for 7 h at 50–60° C. in a Teflon flask. The solvent was removed under vacuum and the residue crystallized in diethyl ether to yield the above compound as a white solid (1.1 g, mp=160° C.). $^1$H NMR (CDCl$_3$):7.49 (2H, m), 7.38 (1H, m), 4.54 (1H, br s), 3.98 (2H, d, J=12 Hz), 3.49 (2H, dd, J$_1$=12 Hz, J$_2$=2.1 Hz), 3.10 (1H, br s).

Example 1

6-[(4-Bromophenyl)methoxy]-2-(3,5-dichlorophenyl)-dihydro-pyrazolo[1,2-α][1,2,4]triazole-1,3-dione

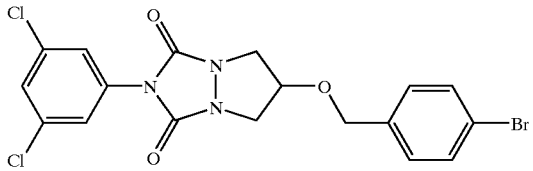

A mixture of 4-(3,5-dichlorophenyl)-[1,2,4]triazolidine-3,5-dione disodium salt (1.5 g, 5.17 mmol) (Preparation 4) and 1-Bromo-4-(2-bromo-1-chloromethyl-ethoxymethyl)-benzene (1.95 g, 5.69 mmol) (Preparation 1) in DMF (25 ml) was heated under reflux for 2 h 30 min. The solvent was removed under vacuum, and water was added to the resulting material. The precipitate was washed with diethyl ether and chromatographed over silica gel (CH$_2$Cl$_2$) to yield the above compound as a white solid (366 mg, mp=142° C.). $^1$H NMR (CDCl$_3$):7.44 (2H, d, J=8.3 Hz), 7.3–7.4 (3H, m), 7.09 (2H, d, J=8.3 Hz), 4.43 (2H, s), 4.15–4.35 (3H, m), 3.49 (2H, dd, J$_1$=12.2 Hz, J$_2$=2.2 Hz).

Example 2

4-Bromobenzoic acid 2-(3,5-dichlorophenyl)-1,3-dioxo-tetrahydro-pyrazolo[1,2-α][1,2,4]triazol-6-yl Ester

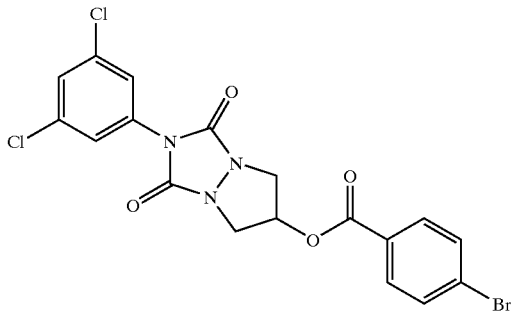

EDCI, HCl (70 mg, 0.37 mmol) and DMAP (4 mg, 0.03 mmol) were added to a solution of 2-(3,5-dichlorophenyl)-6-hydroxy-dihydro-pyrazolo[1,2-α][1,2,4]triazole-1,3-dione (100 mg, 0.33 mmol) (Preparation 6), TEA (92 μl, 0.66 mmol) and 4-bromobenzoic acid (73 mg, 0.36 mmol) in DCM (2 ml). After 72 h at RT, the reaction mixture was washed with a citric acid solution (0.5 M) and a sodium bicarbonate solution, then concentrated. The residue was purified with preparative HPLC to yield the above compound (20 mg). $^1$H NMR (CDCl$_3$):7.71 (2H, d, J=7 Hz), 7.55 (2H, d, J=7 Hz), 7.40 (3H, m), 5.67 (1H, m), 4.34 (2H, d, J=12.7 Hz), 3.80 (2H, dd, J$_1$=12.7 Hz, J$_2$=2.8 Hz).

We claim:
1. A compound having the formula (I),

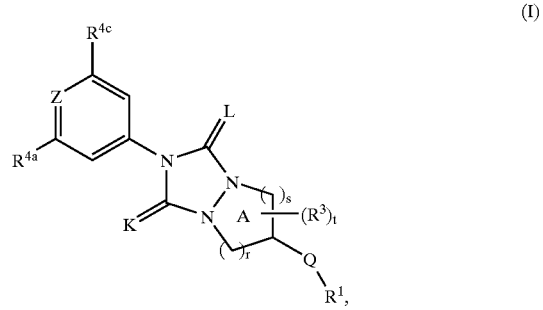

or a pharmaceutically-acceptable salt thereof, in which:
L and K, taken independently, are O or S;
Q is —O—, —NR$^2$—, —S—, —C(=O)—, —CO$_2$—, —OC(=O), —NR$^2$C(=O)—, —C(=O)NR$^2$—, —NR$^2$CO$_2$—, C$_{1-4}$alkylene, C$_{1-4}$substituted alkylene, C$_{2-4}$alkenylene, C$_{2-4}$substituted alkenylene, or optionally-substituted bivalent C$_{1-4}$alkoxy, C$_{1-4}$alkylthio, C$_{1-4}$aminoalkyl, C$_{0-4}$sulfonyl, C$_{0-4}$sulfonamide, C$_{1-4}$acyl, or C$_{1-4}$alkoxycarbonyl,
Z is N or CR$^{4b}$;
R$^1$ is selected from —(CH$_2$)$_n$aryl and —(CH$_2$)$_n$heteroaryl, wherein the aryl and heteroaryl groups are optionally substituted;
R$^2$ is hydrogen or C$_{1-4}$alkyl;
R$^3$ is attached to any available carbon atom of ring A and at each occurrence is independently selected from halogen, alkyl, substituted alkyl, alkenyl, nitro, S(O)$_q$R$^8$, NR$^8$SO$_2$R$^9$, SO$_2$NR$^8$R$^9$, A$_1$—CN, A$_1$—OR$^8$, A$_1$—NR$^8$R$^9$, A$_1$—C(=O)R$^8$, A$_1$—OC(=O)R$^8$, A$_1$—OC(=O)NR$^8$R$^9$, A$_1$—NR$^8$C(=O)R$^9$, A$_1$—NR$^8$C(=O)OR$^9$, A$_2$—CO$_2$R$^8$, and A$_2$—C(=O)NR$^8$R$^9$; or where R$^3$ is attached to a carbon atom other than the Q—R$^1$ substituted carbon atom, R$^3$ may be oxo (=O);
A$_1$ is a bond, —C$_{1-4}$alkylene-, —NHC(=O)—, or —NHC(=O)C$_{1-4}$alkylene-;
A$_2$ is a bond, —C$_{1-4}$alkylene-, —NHC(=O)—, —NHC(=O)C$_{1-4}$alkylene-, —C(=O)— or —C(=O)C$_{1-4}$alkylene-;
R$^{4a}$ R$^{4b}$ and R$^{4c}$ are independently selected from hydrogen, halogen, alkyl, substituted alkyl, alkenyl, substituted alkenyl, nitro, cyano, OR$^6$, NR$^6$R$^7$, NR$^6$C(=O)R$^7$, CO$_2$R$^6$, C(=O)R$^6$, —C(=O)NR$^6$R$^7$, and optionally substituted aryl, heteroaryl, cycloalkyl, and heteroaryl;
R$^6$ and R$^7$ (i) selected independently of each other are hydrogen, alkyl, substituted alkyl, substituted alkenyl, alkoxy, aminoalkyl, or optionally-substituted cycloalkyl, aryl, heteroaryl, or heterocyclo; or (ii) taken together form a heterocyclo;
R$^8$ and R$^9$ (i) selected independently of each other are hydrogen, alkyl, substituted alkyl, alkenyl, substituted alkenyl, alkoxy, or optionally-substituted cycloalkyl, aryl, heteroaryl, or heterocyclo; or (ii) taken together form a heterocyclo;

n is 0, 1, 2, 3 or 4;

q is 0, 1, or 2;

r and s are 0, 1, or 2, provided that r+s=2; and t is 0, 1, or 2.

2. The compound of claim 1, or a pharmaceutically-acceptable salt thereof, in which:

$R^3$ is attached to the Q—$R^1$ substituted carbon atom;

Q is —O—, —NH—, —S—, —OC(=O), —NHC(=O)—, or —NHCO$_2$—; and $A_1$ and $A_2$ are selected from a bond and $C_{1-4}$alkylene.

3. The compound of claim 1, or a pharmaceutically-acceptable salt thereof, in which $R^{4a}$, $R^{4b}$ and $R^{4c}$ are independently selected from hydrogen, halogen, alkyl, haloalkyl, nitro, cyano, OH, O(alkyl), haloalkoxy, O-phenyl, —CO$_2$H, —C(=O)H, NH$_2$, NH(alkyl), N(alkyl)$_2$, CO$_2$alkyl, C(=O)alkyl, alkylthio, —C(=O)NH(CHR$^{15}$)$_{1-2}$CO$_2$H, —C(=O)NH(CHR$^{15}$)$_{1-2}$CO$_2$(alkyl), phenyl, pyrrolyl, pyridinyl, and isoxazolyl, wherein each of the phenyl, pyrrolyl, pyridinyl and isoxazolyl groups are optionally substituted with one to two halogen, $C_{1-4}$alkyl, OMe, haloalkyl, CN, haloalkoxy, CO$_2$H, —C(=O)H, CO$_2$alkyl, and/or C(=O)alkyl; and $R^{15}$ is hydrogen or optionally-substituted $C_{1-4}$alkyl.

4. The compound of claim 2 in which $R^{4a}$ and $R^{4c}$ are both halogen.

5. The compound of claim 1, or a pharmaceutically-acceptable salt thereof, in which $R^1$ is unsubstituted aryl or aryl having one to two substituents selected from halogen, alkyl, haloalkyl, nitro, cyano, OR$^{10}$, NR$^{10}$R$^{11}$, CO$_2$R$^{10}$, C(=O)R$^{10}$, C(=O)NR$^{10}$R$^{11}$, NR$^{10}$C(=O)R$^{11}$, NR$^{10}$C(=O)OR$^{11}$, S(O)$_p$R$^{10}$, NR$^{10}$SO$_2$R$^{11}$, SO$_2$NR$^{10}$R$^{11}$, aryl, cycloalkyl, and heteroaryl;

$R^{10}$ and $R^{11}$ (i) selected independently of each other are hydrogen, alkyl, substituted alkyl, substituted alkenyl, alkoxy, or optionally-substituted cycloalkyl, aryl, heteroaryl, or heterocyclo; or (ii) taken together form a heterocyclo; and p is 0, 1 or 2.

6. The compound of claim 1, or a pharmaceutically-acceptable salt thereof, in which $R^{4a}$ and $R^{4c}$ are halogen and Z is CH.

7. The compound of claim 1, or a pharmaceutically-acceptable salt thereof, in which Q is —C(=O), —OC(=O)—, bivalent alkoxy, —NHC(=O)—, —C(=O)NH, or —NHCO$_2$—, and $R_1$ is aryl or heteroaryl optionally substituted with halogen, $C_{1-4}$alkyl, CO$_2$H, CO$_2$(alkyl), NH$_2$, NH(alkyl), N(alkyl)$_2$, and/or oxo (=O).

8. The compound of claim 1, or a pharmaceutically-acceptable salt thereof, in which Q is —OC(=O)— or —O(CH$_2$)$_{1-2}$— and $R_1$ is phenyl optionally substituted with one to two substituents selected from halogen, cyano, nitro, haloalkyl, haloalkoxy, hydroxy, $C_{1-4}$alkoxy, —CO$_2$H, —C(=O)H, amino, and $C_{1-4}$aminoalkyl.

9. The compound of claim 3, having the formula, in which $R^{4a}$ and $R^{4c}$ are halogen; $R^5$ is hydrogen, halogen, alkyl, trifluoromethyl, OCF$_3$, nitro, or cyano; and t is 0 or 1.

10. The compound of claim 1, selected from (i)
6-[(4-Bromophenyl)methoxy]-2-(3,5-dichlorophenyl)-dihydro-pyrazolo[1,2-α][1,2,4]triazole-1,3-dione;
4-Bromobenzoic acid 2-(3,5-dichlorophenyl)-1,3-dioxo-tetrahydro-pyrazolo[1,2-α][1,2,4]triazol-6-yl ester;
6-[(4Cyanophenyl)methoxy]-2-(3,5-dichlorophenyl)-dihydro-pyrazolo[1,2-α][1,2,4]triazole-1,3-dione;
4-Cyanobenzoic acid 2-(3,5-dichlorophenyl)-1,3-dioxo-tetrahydro-pyrazolo[1,2-α][1,2,4]triazol-6-yl ester; and
(ii) pharmaceutically-acceptable salts thereof.

11. A compound having the formula, or a pharmaceutically-acceptable salt thereof, in which:

K and L are independently O or S;

Q is —O—, —NH—, —S—, —CO$_2$—, —C(=O)—, —OC(=O), —NHC(=O)—, —C(=O)NH—, —NHCO$_2$—, $C_{1-4}$alkylene, $C_{1-4}$substituted alkylene, $C_{2-4}$alkenylene, $C_{2-4}$substituted alkenylene, or optionally-substituted bivalent $C_{1-4}$alkoxy, $C_{1-4}$alkylthio, $C_{1-4}$aminoalkyl, $C_{0-4}$sulfonyl, $C_{0-4}$sulfonamide, $C_{1-4}$acyl, or $C_{1-4}$alkoxycarbonyl;

Z is N or CR$^{4b}$;

$R^1$ is aryl or heteroaryl optionally substituted with one to two substituents selected from halogen, alkyl, substituted alkyl, nitro, cyano, OR$^{10}$, NR$^{10}$R$^{11}$, CO$_2$R$^{10}$, C(=O)R$^{10}$, C(=O)NR$^{10}$R$^{11}$, NR$^{10}$C(=O)R$^{11}$, NR$^{10}$C(=O)OR$^{11}$, S(O)$_p$R$^{10}$, NR$^{11}$SO$_2$R$^{10}$, SO$_2$NR$^{10}$R$^{11}$, —NHCH(alkyl)CO$_2$R$^{10}$, aryl, cycloalkyl, and heteroaryl;

$R^3$ is attached to any available carbon atom of ring A and at each occurrence is independently selected from halogen, alkyl, substituted alkyl, alkenyl, nitro, S(O)$_q$R$^8$, NR$^9$SO$_2$R$^8$, SO$_2$NR$^8$R$^9$, $A_1$—CN, $A_1$—OR$^8$, $A_1$—NR$^8$R$^9$, $A_1$—C(=O)R$^8$, $A_1$—OC(=O)R$^8$, $A_1$—OC(=O)NR$^8$R$^9$, $A_1$—NR$^8$C(=O)R$^9$, $A_1$—NR$^8$C(=O)OR$^9$, $A_2$—CO$_2$R$^8$, and $A_2$—C(=O)NR$^8$R$^9$;

or where $R^3$ is attached to a carbon atom other the $Q-R^1$ substituted carbon atom, $R^3$ may be oxo (=O);

$A_1$ is a bond, $-C_{1-4}$alkylene-, $-NHC(=O)-$, or $-NHC(=O)C_{1-4}$alkylene-;

$A_2$ is a bond, $-C_{1-4}$alkylene-, $-NHC(=O)-$, $-NHC(=O)C_{1-4}$alkylene-, $-C(=O)-$ or $-C(=O)C_{1-4}$alkylene-;

$R^{4a}$ and $R^{4c}$ are halogen, alkyl, cyano, trifluoromethyl, or nitro;

$R^{4b}$ is hydrogen, halogen, alkyl, substituted alkyl, nitro, cyano, hydroxy, alkoxy, phenyloxy, $-CO_2H$, $-C(=O)H$, amino, NH(alkyl), N(alkyl)$_2$, $CO_2$alkyl, $C(=O)$alkyl, alkylthio, $-C(=O)NH(CH_2)_{1-4}CO_2H$, $-C(=O)NH(CH_2)_{1-4}CO_2$(alkyl), aryl, heteroaryl, or heterocycle, wherein each of the aryl, heteroaryl, and heterocycle groups are optionally substituted with one to two halogen, $C_{1-4}$alkyl, OMe, $CF_3$, CN, $OCF_3$, $CO_2H$, $-C(=O)H$, $CO_2$alkyl, or $C(=O)$alkyl;

$R^6$ and $R^7$ (i) selected independently of each other are hydrogen, alkyl, substituted alkyl, substituted alkenyl, alkoxy, or optionally-substituted cycloalkyl, aryl, heteroaryl, or heterocyclo; or (ii) taken together form a heterocyclo ring;

$R^8$ and $R^9$ (i) selected independently of each other are hydrogen, alkyl, substituted alkyl, substituted alkenyl, alkoxy, or optionally-substituted cycloalkyl, aryl, heteroaryl, or heterocyclo except $R^8$ is not hydrogen when attached to a sulfonyl group as in $S(=O)R^8$ or $S(O)_2R^8$; or (ii) taken together form a heterocyclo ring;

$R^{10}$ and $R^{11}$ (i) selected independently of each other are hydrogen, alkyl, substituted alkyl, substituted alkenyl, alkoxy, or optionally-substituted cycloalkyl, aryl, heteroaryl, or heterocyclo except $R^{10}$ is not hydrogen when attached to a sulfonyl group as in $S(=O)R^{10}$ or $S(O)_2R^{10}$; or (ii) taken together form a heterocyclo;

p and q are independently 0, 1, or 2;

r is 1 or 2; and t is 0, 1 or 2.

12. The compound of claim 11, or a pharmaceutically-acceptable salt thereof, in which K and L are O;

Q is $-O-$, $-CO_2-$, $-OC(=O)-$, -or bivalent alkoxy;

Z is $CR^{4b}$;

$R^1$ is optionally-substituted phenyl;

$R^{4a}$ and $R^{4c}$ are halogen; and $R^{4b}$ is hydrogen.

13. The compound of claim 12, or a pharmaceutically-acceptable salt thereof, in which $R_1$ is

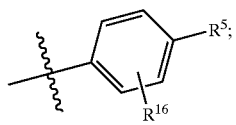

$R^5$ is halogen, cyano, nitro, trifluoromethyl, or $OCF_3$, and $R^{16}$ is hydrogen, halogen, lower alkyl, cyano, nitro, $-CO_2H$, $-C(=O)H$, $CO_2$alkyl, or $-C(=O)$alkyl.

14. A compound having the formula,

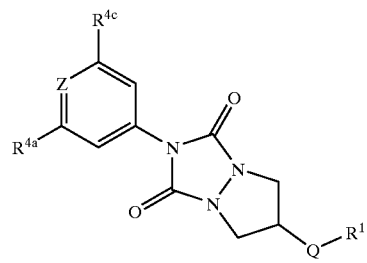

or a pharmaceutically-acceptable salt thereof, in which:

Q is $-O-$, $-OC(=O)$ or optionally-substituted bivalent $C_{1-4}$alkoxy;

Z is N or $CR^{4b}$;

$R^1$ is hydrogen, alkylsilyl, or phenyl optionally substituted with one to two substituents selected from halogen, $C_{1-4}$alkyl, hydroxy, alkoxy, haloalkoxy, haloalkyl, cyano, and nitro; and $R^{4a}$, $R^{4b}$, and $R^{4c}$ are independently selected from halogen, $C_{1-4}$alkyl, haloalkyl, haloalkoxy, cyano, and nitro.

15. A pharmaceutical composition comprising (a) at least one compound according to claim 1, or a pharmaceutically acceptable salt thereof, and (b) a pharmaceutically acceptable carrier or diluent.

16. A pharmaceutical composition adapted for treating an inflammatory or immune disease comprising (i) at least one compound of claim 1 or a pharmaceutically acceptable salt thereof; (ii) one or more second compounds effective for treating an inflammatory or immune disease; and (iii) a pharmaceutically-acceptable carrier.

17. A pharmaceutical composition comprising (a) at least one compound according to claim 11, or a pharmaceutically acceptable salt thereof, and (b) a pharmaceutically acceptable carrier or diluent.

18. A method of inhibiting LFA-1/ICAM interactions in a mammal comprising administering to the mammal a therapeutically-effective amount of a compound according to claim 1.

19. A method of treating an inflammatory or immune disease in a mammal animal comprising administering to the mammal in need of such treatment a therapeutically-effective amount of a pharmaceutical composition according to claim 17.

20. The method of claim 19 in which the inflammatory or immune disease is selected from hypogonadism, frailty, osteoporosis, sexual dysfunction, wasting, anemia, cancers of the breast, brain, skin, ovary, endometrium, bladder, prostate, lung, colon, lymphatic system, liver and kidney, hirsutism, Alzheimer's disease, non-insulin dependent diabetes mellitus, acne, seborrhea, alopecia, fibroids, hyperpilosity, cachexia, polycystic ovarian syndrome, anorexia, contraception, drug withdrawal syndrome, pregnancy termination, and benign prostate hypertrophy.

* * * * *